(12) United States Patent
Tinker et al.

(10) Patent No.: US 6,492,570 B1
(45) Date of Patent: Dec. 10, 2002

(54) METALLACARBORANES

(75) Inventors: Nigel Dennis Tinker, Cheshire (GB); Kenneth Wade, Durham (GB); Thomas Gibson Hibbert, Durham (GB)

(73) Assignee: British Nuclear Fuels PLC (GB)

( * ) Notice: Subject to any disclaimer, the term of this patent is extended or adjusted under 35 U.S.C. 154(b) by 0 days.

(21) Appl. No.: 09/297,790

(22) PCT Filed: Nov. 7, 1997

(86) PCT No.: PCT/GB97/02992

§ 371 (c)(1),
(2), (4) Date: Dec. 13, 1999

(87) PCT Pub. No.: WO98/21216

PCT Pub. Date: May 22, 1998

(30) Foreign Application Priority Data

Aug. 11, 1996 (GB) ............................................. 9623311

(51) Int. Cl.[7] .............................. C07F 19/00; C07F 7/28; C07F 15/00; C07F 15/06; B01J 31/00

(52) U.S. Cl. ....................... 585/275; 585/277; 585/250; 502/154; 502/155; 502/171; 502/202; 502/204; 502/207; 502/223

(58) Field of Search ................................ 585/275, 277, 585/250; 502/154, 155, 171, 202, 204, 207, 223

(56) References Cited

U.S. PATENT DOCUMENTS 5,462,724 A * 10/1995 Schinazi et al. ........... 424/1.77

OTHER PUBLICATIONS

Carr et al.; *Carborane Complexes of Nickel and Platinum: Synthesis and Protonation Reactions of Anionic Allyl (carborane) Species*, Chemical Abstracts 121:1 Abstract No. 9646q (Jul. 4, 1994).

Gomez et al.; *Synthesis and Structural Characterization of Metallacarboranes Containing Bridged Dicarbollide Ligands*, Chemical Abstracts 117:11 Abstract No. 111670x (Sep. 14, 1992).

Zakharkin et al.; *Synthesis of Binuclear Rhodacarboranes from 1,4–and 1,3–$C_6H_4(CH_2$–9–$C_2H_2B_9H_9$–7, 8–nido)22–dianions and ($Ph_3P$) $3RhCl$* Chemical Abstracts 126:6 Abstract No. 75044w (Feb. 10, 1997).

International Search Report, PCT/GB97/02992.

Fronczek et al., "The Synthesis, Crystal Structure, and Reactions of an Actinide Metallocarborane Complex, Bis ($\eta^5$–(3)–1,2–Dicarbollyl)Dichlorouranium (IV) Dianion, $[U(C_2B_9H_{11})_2Cl_2]^{2-1a}$", *Journal of the American Chemical Society*, 99:6, pp.1769–1775, Mar. 16, 1977.

Hawthorne et al., "Search for Cluster Catalysis with Metallacaranes", *Cluster Catalysis with Metallacarboranes*, pp.225–233, (1988).

Plešek et al., "Constitution and HPLC Resolution of Enantomers of the $[8,4'–\mu–R_2N–commo–(1,2–C_2B_9H_{10})_2–3–Co]$ Complex–The Third Isomer of Nitrogen–Bridged Bisicosahedral Cobaltacarborane", *Collect. Czech. Chemical Communications*, vol. 59, pp.374–381, (1984).

* cited by examiner

Primary Examiner—Bekir L. Yildirim
(74) Attorney, Agent, or Firm—Myers Bigel Sibley & Sajovec, P.A.

(57) ABSTRACT

The invention provides a polynuclear compound comprising two or more metal-hapto-3-capped nidocarborane groups. Also provided is the use of such a compound as a catalyst in a chemical reaction such as a hydrogenation or oxidation reaction.

18 Claims, 5 Drawing Sheets

"Z- Compound"

"Meta-Z-Compound"

"Tetrathallium salt of <u>A</u>"

"Tetrathallium salt of <u>B</u>"

METALLACARBORANES

CROSS-REFERENCE TO RELATED APPLICATIONS

Figure 1:
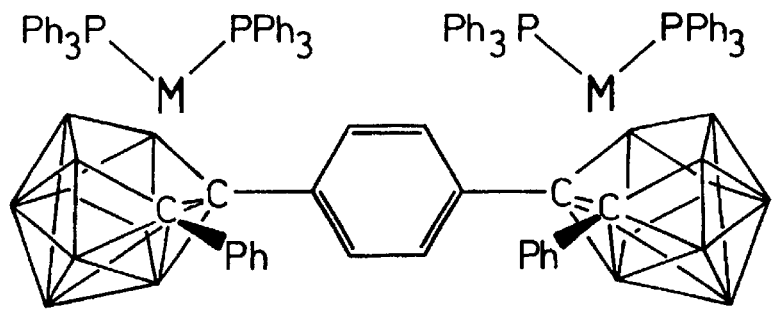

The present application is the U.S. national phase application of PCT International Application No. PCT/GB97/02992, having an international filing date of Nov. 7, 1997 and claiming priority to Great Britain Application No. 9623311.9 filed Aug. 11, 1996, the disclosures of which are incorporated herein by reference in their entireties. The above PCT International Application was published in the English language and has International Publication No. WO 98/21216.

INTRODUCTION

This invention relates to metallacarboranes and to the use of metallacarboranes in the a of catalysis.

A carborane is a mixed hydride of boron and carbon containing a polyhedral framework of boron atoms which also includes one or more carbon atom. There are several classes of carboranes, two of which are of particular importance, the closo and nido categories. The prefix closo is used to designate those carboranes in which the framework is a complete deltahedron. The prefix nido designates those frameworks which are "open", that is, one deltahedral site is incomplete.

Polyhedral closocarboranes have the formula $B_{n-2}C_2H_n$ ($n \geq 5$) and they may be prepared in a variety of ways. By way of examples reference will be made to dicarba-coso-dodecaboranes. 1,2-, 1,7- and 1,12-isomers exist, known respectively as ortho-caborane, meta-carborane and para-carborane. Icosahedral carboranes have high thermal stabilities, they are air stable and exhibit considerable chemical robustness.

Ortho-carboranes, $R_2C_2B_{10}H_{10}$, may be prepared by reaction of decaborane adducts, $B_{10}H_{12}L_2$ (where L=dms, acetonitrile), with the appropriately substituted acetylene ($RC\equiv CR^1$).

Meta-carborane can be prepared quantitatively by thermal isomerisation of ortho-carborane at 460° C., while para-carborane may be obtained by thermal isomerisation of the meta-isomer at 620° C. However, the high temperatures required for these isomerisations render them unsuitable as routes to most substituted carboranes and alternative routes to substituted meta- and para-carboranes are used.

The hydrogen atoms on the carbons of dicarba-closo-dodecaboranes are acidic and thus undergo reaction with organolithium reagents (such as butyllithium) to produce C-lithiated carboranes. This carboranyl carbon lithium bond is itself susceptible to electrophilic attack, providing a means of preparing substituted meta- and para-carboranes. Carboranyl Grignard agents and copper derivatives can be prepared and used in a similar manner.

Other sigma-bonded carborane metal complexes have been reported in the literature, especially complexes of transition metals. F-block metal complexes have been reported but only with lanthanum, terbium and ytterbium as well as tentative reports of complexes with samarium and europium. No sigma-bonded actinide systems have been reported. Both 1,2- and 1,7-$B_{10}C_2H_{12}$ can be degraded by strong bases to give isomeric $B_9C_2H_{12}$ ions. This removal of a $BH^{2+}$ unit from the parent carborane can be considered to result from nucleophilic attack at the most electron-deficient boron atom of the carborane. The $B_9C_2H^-_{12}$ ions can be protonated to form the neutral nidocarborane, $B_9C_2H_{13}$, which is a strong acid.

There are also many literature reports of pi-bonded metallacarboranes, again with transition metals. An actinide complex is reported by Fronczek et al in JACS, 99:6 1977 at page 1769. This results from the reaction of $UCl_4$ with the $B_9C_2H_{11}^{2-}$ anion in tetrahydrofuran solution and inert atmosphere conditions. The complex anion $[U(B_9C_2H_{11})_2Cl_2]^{2-}$ has been isolated as several air-sensitive crystalline salts.

An $NR_2$ bridged system has been reported by Plesek in Collect. Czech Chem Comm, vol 59, 1994 at page 374. An asymmetric cobaltacarborane complex is described which contains a monoatomic nitrogen bridge between both carborane units.

Figure 9A:
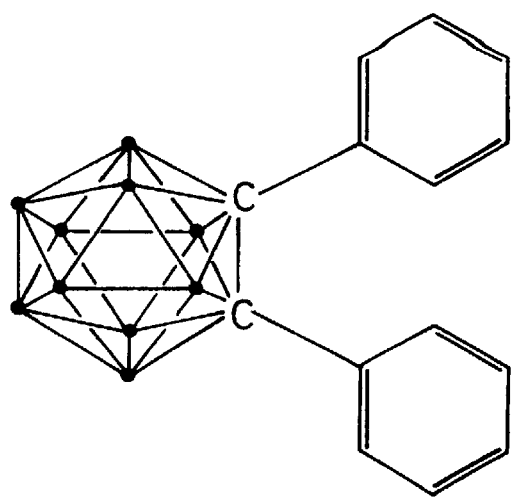

In addition to the carborane monomers mentioned above, substituted monomers may be prepared, an example being as shown in accompanying FIG. 9A.

Figure 9B:
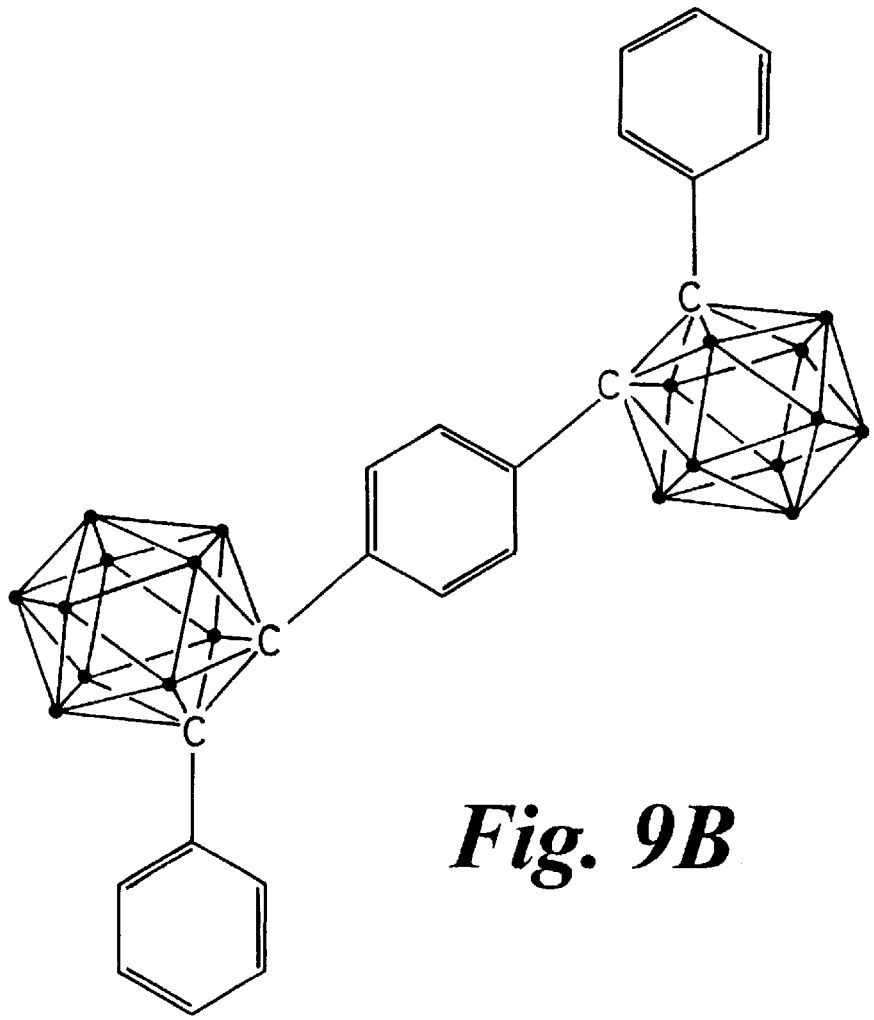

Furthermore, oligomer structures have been prepared. By way of example, a structure having two carborane units is illustrated in FIG. 9B.

Figure 9C:
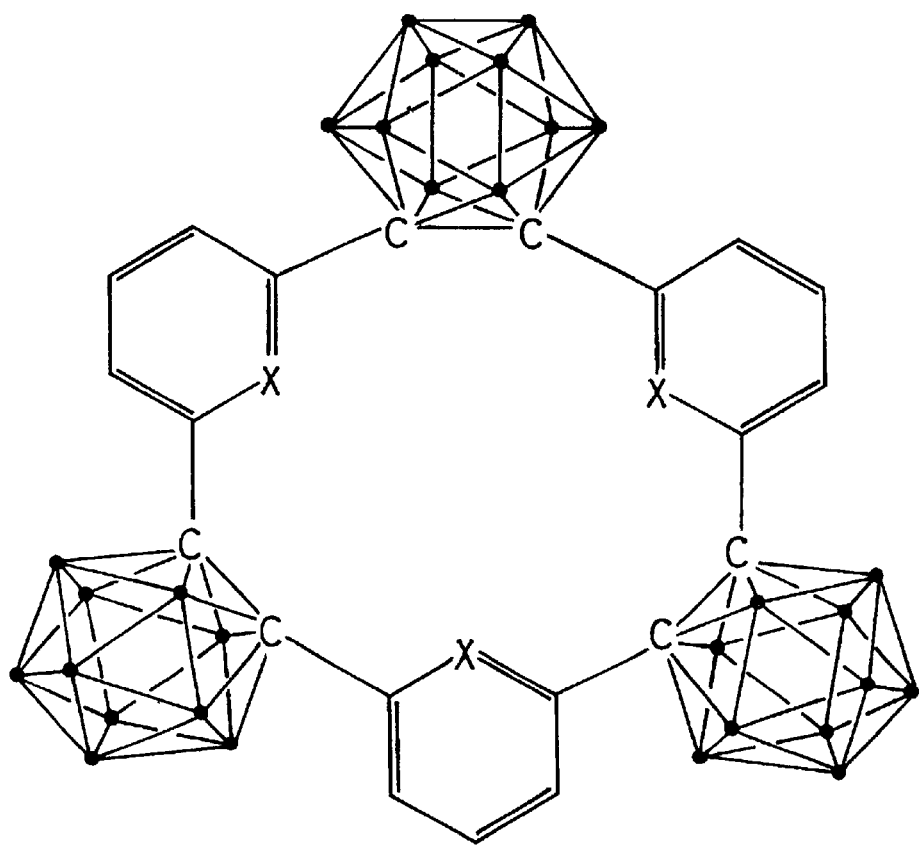
Figure 9D:
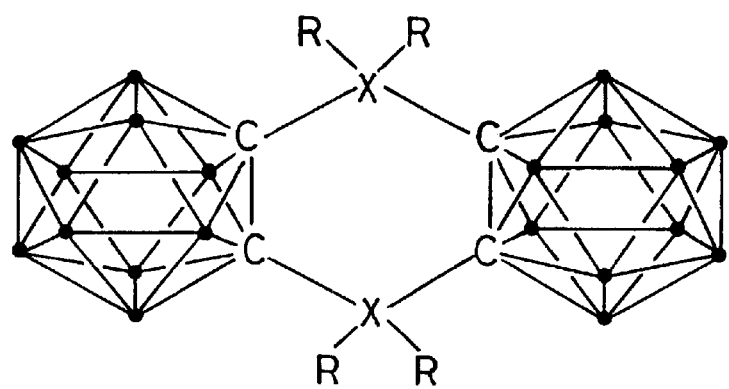

In addition, cyclic structures are known. Cyclic oligomers include dimer and trimer systems in particular, but higher ring sizes may be possible. The compounds shown in FIGS. 9C (where X is CH or N) and FIG. 9D (where X is Si, Sn or As) represent examples of cyclic structures.

In general, metals can be sandwiched between two nido anions or linked to just one anion to produce an "open sandwich". An open sandwich structure leaves the remainder of the metal coordination available for occupation by other ligands. For example, certain RH(III) clusters have been disclosed by M F Hawthorne in Mol. Struct.Energ., vol 5, 1988, page 225 as homogeneous catalyst precursors for alkene isomerization or hydrogenation.

SUMMARY OF INVENTION

According to the present invention there is provided a polynuclear compound comprising two or more metal-hapto-3-capped nidocarborane groups. Preferably, a compound of the invention has at least one other real coordination site filled by a monodentate ligand.

Preferably, the compound of the invention has a cyclic structure.

Preferably, a compound of the invention includes two or three nidocarborane groups.

One class of compounds comprises oligomers of the polynuclear compounds. ie a chain of two or more of the polynuclear compounds of the invention, suitably linked by the reaction together of chemically reactive groups on subsituents of the nidocarborane units.

A preferred compound in accordance with the present invention is one in which two or more nidocarborane groups are linked together by a phenyl, pyridyl, triazyl, B(OH), CO, SO, $CH_2$ or B(Ph) group, such that linear or cyclic structures are formed. The cyclic structures may have metals coordinated in the central cavity.

Preferred compounds contain a metal taken from F block metals, Rh, Co, Mn, Ru, Pd, W, Fe, Ni, Pt, Cr or Mo, and may contain the same metal at each site or different metals at each site.

A preferred metallacarborane includes two or more carborane units linked by means of a benzene ring, a pyridine ring or a triazine ring.

Preferably, the carborane units are functionalised (ie substituted) or linked in the 1,3, 1,4 or 1,5 (ie ortho, meta or para) positions. For functionalised carborane units, various substituent groups can be used including phenyl, alkyl (eg methyl) or a group (eg containing a phenyl or alkyl residue)

having a reactive factional group (eg —COOH, an ester or an unsaturated group such as an ethylenic double bond). The functionalisation may or may not be symmetrical.

For the linkages within the linear or cyclic polynuclear compounds, particularly preferred units include phenyl (connected meta or para), pyridine, CO, SO, $CH_2$ and $B(OH)$.

The present invention also provides a method of carrying out a chemical reaction in which a compound of any of the preceding claims acts as a catalyst in the reaction. Compounds of the invention may be of use in, for instance, hydrogenation, isomerisation, polymerisation and oxidation reactions. For instance, a compound of the invention in which the metal is Rhodium may be used as a hydrogenation catalyst and a compound of the invention in which the metal is Uranium may be used as an oxidation catalyst.

DESCRIPTION OF EMBODIMENTS

Examples of embodiments of the present invention will now be described with reference to FIGS. 1 to 8 of the accompanying drawings. FIGS. 1 to 3 and 5 to 8 illustrate 1,3 substituted compounds; their 1,4 and 1,5 substituted analogues as well as the corresponding unsubstituted compounds are of course included in the invention, as are the substituted variants of the FIG. 4 compounds. The compounds shown in FIG. 8 were prepared as follows:

Preparation of Carborane Compounds

1) Preparation of 8A: 'Z-Compound'—1,4-bis (phenylorthocarboranyl)benzene 5.37 g (19.29 mmol) of 1,4-bis(phenylethynyl)benzene was partially dissolved in 50 ml of dry toluene, leaving a white slurry. 15.37 g (62.96 mmol) of $B_{10}H_{12}$ $(DMS)_2$ was added to the toluene slurry, which was then slowly heated. As the reaction reached 55–65° C., effervescence was noticed and after this subsided the reaction was heated to 90° C. At this point the solution was yellow and contained a small amount of white solid. The reaction was kept at 90° C., with periodic venting to remove nascent dms. The reaction was run for 45 hrs. Removal of the toluene left a sticky solid to which was added 80 ml of methanol. The flask was then heated to 80° C. and refluxed for 21 hours. The white solid was removed by filtration and washed with chilled methanol. The product was recrystallized from cyclohexane—yield 77%.

2) Preparation of 8C:—Tetrathallium Salt of 8A 0.598 g (0.99 mmol) of 1,4-bis(phenylorthocarboranyl) benzene and 0.583 g of 85% KOH pellets (8.85 mmol) were placed in a flask under $N_2$ and 40 ml of methanol was added. The reaction was then refluxed (80° C.) for five days. The unreacted para-bis(phenylorthocarboranyl)benzene was removed by filtration and the filtrate was cooled to room temperature 0.501 g (1.90 mmol) of TlOAc was dissolved in 10 ml of water and added to the filtrate, precipitating an off-white solid. After stirring overnight (15 hours) the cream solid was removed by filtration and washed with water. Yield 70%.

3) Preparation of 8B:—'Meta-Z-Compound' 1,3-di (phenylorthocarboranyl)benzene 8.51 g 1,3-di(phenylethynyl)benzene and 12.0 g (a 50% excess) of $B_{10}H_{12}DMS_2$ were suspended in 60 ml toluene which was then refluxed at 90° C. for 7 days. After cooling, the solvent was removed and 60 ml MeOH was added and reflux was resumed for a further 18 hours. Removal of MeOH, left the crude product, which was recrystallized from benzene. Yield 44%.

4) Preparation of 8D:—Tetrathallium Salt of 8B

This compound was prepared in the same way as Compound C.

Preparation of Metallacarboranes

Figure 8A:
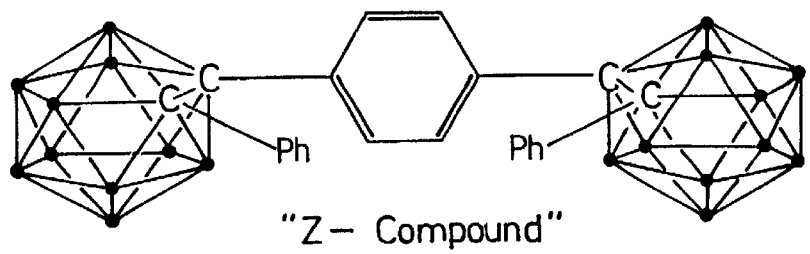
Figure 8B:
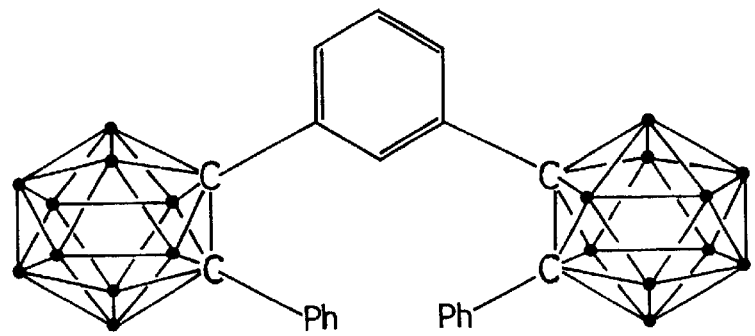
Figure 8C:
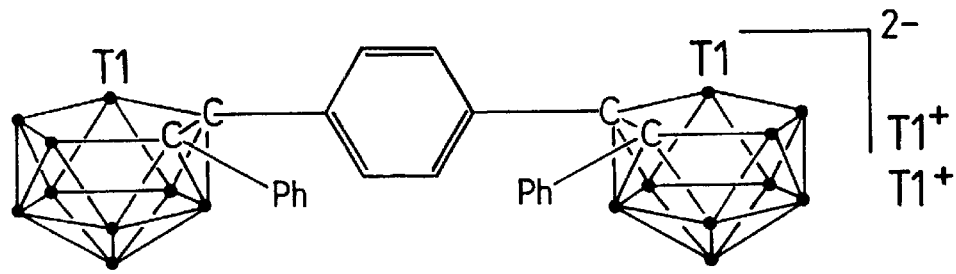
Figure 8D:
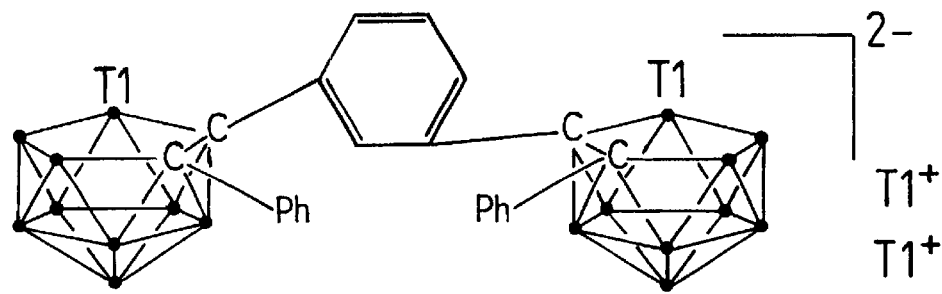

1) Compounds of the type shown in FIG. 1 were prepared by the reaction of the tetrathallium salt of "Z compound" shown in FIG. 8C with two equivalents of $(Ph_3P)_2HCl_2$ (where M=Pt, Pd, Co, Ni) in dry THF at room temperature under dry nitrogen conditions for 1 hour (reaction appeared to be complete after about 10 minutes). The TlCl precipitated, leaving the desired product in solution. This air-stable product was filtered and pumped to dryness in vacuo giving yields of 40–75%. Compounds were characterised by IR, NMR, elemental analysis, mass spectrometry and magnetic measurements.

By way of example, $Tl_4$ $[1,4-(1-C_6H_5—C_2B_9H_9)_2C_6H_4]$ (328 mg, 0.25 mmol) was suspended in stirred thf (40 ml) under ambient conditions, and brown $(PPh_3)_2CoI_2$ (420 mg, 0.50 mmol) was added. This immediately caused the formation of an off-white precipitate (Thallium (I) iodide), which turned grey on standing in air. After 30 minutes stirring, the bright green solution was isolated by filtration and the thf removed in vacuo, yielding Bis-Co $(PPh_3)_2$-1,4-$(1-C_5H_5—C_2B_9H_9)_2C_6$.

Appearance: Bright green powder

Yield: 311 mg, 75%

IR (KBr disc; $v_{max}$): 3052 w (phenyl CH stretch), 3026 vw (phenyl CH stretch), 3000 vw (phenyl CH stretch), 2962 vw (phenyl CH stretch), 2511 s,br (BH stretch), 1479 m (C=C stretch), 1435 s (C=C stretch), 1155 m (P—C stretch), 1121 s (phenyl i.p.def.), 1094 s (phenyl i.p.def.), 1070 m (phenyl i.p.def.), 743 s (phenyl o.o.p.def.), 725 m (phenyl o.o.p.def.), 693 vs (B—H stretch), 593 m (C—H wag)

Molar Magnetic Susceptibility ($\chi M$): 2.71 BM

E.A. Found C, 67.7; H, 5.5; $C_{94}H_{92}B_{18}P_4Co_2$ requires C, 68.1; H, 5.6.

Figure 2:
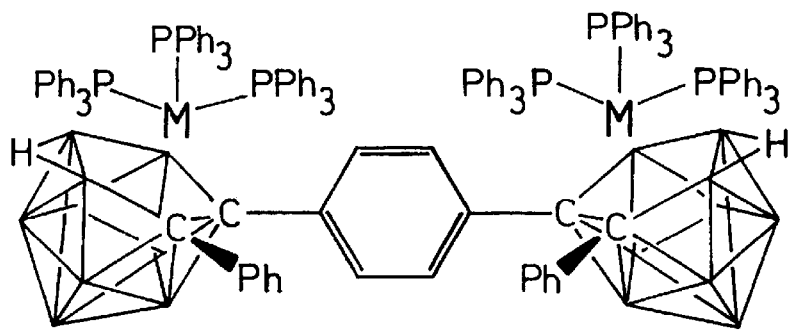

2) The compound shown in FIG. 2 where M is Rh was prepared by reaction of the bis-potassium salt of the Z compound with two equivalents of $(Ph_3P)_3RhCl$ in dry MeOH at room temperature under nitrogen conditions for 1 hour. The precipitate KCl was removed by filtration and the solution pumped to dryness to give the product in approximately 80% yield. Chacterisation was as for the FIG. 1 compounds.

More specifically, $K_2$ $[1,4-(1-C_6H_5—C_2B_9H_{10})_2C_6H_4]$ (448 mg, 0.15 mmol) was suspended in stirred thf (40 ml) under ambient conditions, and $(PPh_3)_3RhCl$ (277 mg, 0.30 mmol) was added. This immediately caused the formation of a white precipitate (TlCl), which turned grey on prolonged standing in air. After 30 minutes stirring, the orange solution was isolated by filtration and the thf removed in vacuo, yielding Bis-Rh$(PPh_3)_3$-1,4-$(1-C_6H_5—C_2B_9H_{10})_2C_6H_4$.

Appearance: Orange/red powder

Yield: 265 mg, 78%

IR (KBr disc; $v_{max}$): 3053 w (Phenyl CH stretch), 3022 vw (phenyl CH stretch), 2962 vw (phenyl CH stretch), 2517 s,br (BH stetch), 1482 m (C=C stretch), 1435 s (C=C stretch), 1191 s (P-C stretch), 1119 s (phenyl i.p.def.), 1093 m (phenyl i.p.def.). 1069 m (phenyl i.p.def.), 747 m (phenyl o.o.p.def.), 721 s (phenyl o.o.p.def.), 694 vs (BH stretch), 542 vs (C—H wag), 519 m (C—H wag).

NMR ($C_6D_6$): $^1H$ δ 0.7–3.5 ppm (v.broad multiplet, B H), 7.4–7.7 (complex: multiplet of multiplets, phenyl CH), $^{31}P$ δ=ppm 25.12 (s, free PPh$_3$), 30.72 (doublet of doublets, $J_a$=146 Hz $J_b$=38 Hz, bound PPh$_3$), 47.6 (doublet of triplets, $J_a$=191 Hz $J_b$=37 Hz, bound PPh$_3$), 52.34 (d, J=195 Hz, bound PPh$_3$).

E.A. C, 66.3; H, 5.5; $C_{130}B_{18}H_{124}P_6Rh_2$ requires C, 68.2; H, 5.5.

Figure 3:
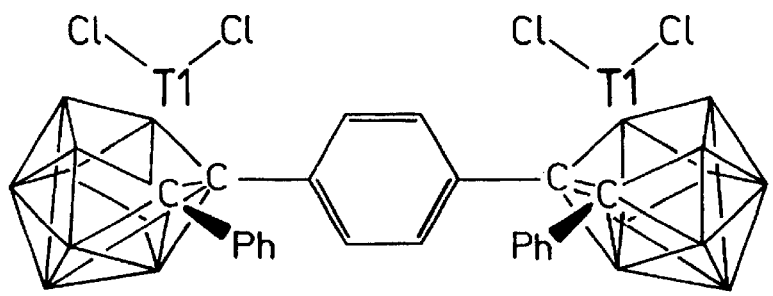

3) The compound shown in FIG. 3 was prepared by the reaction of the Z compound with 2 equivalents of $TiCl_4$ under nitrogen in dry THF at −78° C. for 15 minutes. The precipitated TlCl was separated by room temperature filtration and the desired product was obtained by removal of the solvent at 78% yield. Characterisation was as for the compounds of FIG. 1.

More specifically, $Tl_4$ [1,4-(1-$C_6H_5$—$C_2B_2H_9)_2C_6H_4$] (263 mg, 0.20 mmol) was suspended in stirred thf (40 ml) under dry $N_2$ conditions, and $TiCl_4$ (77 mg, 0.41 mmol) was added. This immediately caused the formation of a white precipitate (TlCl), which turned grey on prolonged standing in air. After 30 minutes stirring, the red solution was isolated by filtration and the thf removed in vacuo, yielding Bis-$TlCl_2$-1,4-(1-$C_6H_5$—$C_2B_9H_9)_2C_6H_4$.

Appearance: Brick red powder
Yield: 115 mg, 79%
IR (KBr disc; $v_{max}$): 3020 w (phenyl CH stretch), 2956 w phenyl CH stretch), 2935 vw (phenyl CH stretch). 2524 vs,br (BH stretch), 1470 s (C═C stretch), 1444 s,br (C═C stretch), 1115 s (phenyl i.p.def.), 1016 m (phenyl o.p.def.), 719 vs,br (BH stretch), 648 m (phenyl o.o.p.def.), 620 m (phenyl o.o.p.def.), 550 m (C—H wag).
NMR ($C_6D_6$): $^1H$ δ=1.0–4.0 ppm (v. broad multiplet, B H), 7.47 broad multiplet, phenyl CH); $^{11}B$ δ c. −40—+20 ppm (extremely broad signal, BH).
E.A. Found C, 27.5; H, 3.2; $C_{22}B_{12}H_{32}Cl_4Ti_2$ requires C, 25.8; H, 3.2.

Figure 4:
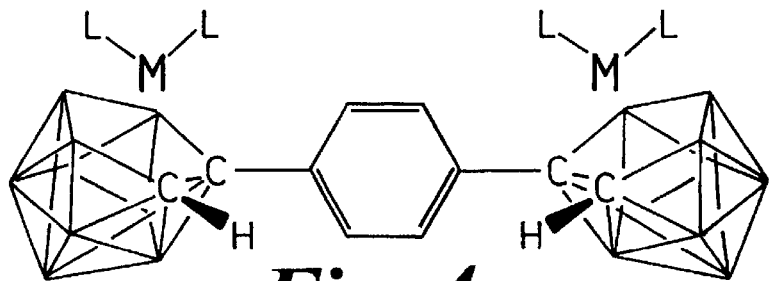

4) Compounds of the type shown in FIG. 4 (where M is Zr, L is Cl, M is Zr, L is Cp, and M is Ti) were prepared by the reaction of the tetrathallium salt of 1,4-bis orthocarboranyl benzene with two equivalents of $Cp_xMCl_{4-x}$ in dry THF at 78° C. under nitrogen for approximately 30 minutes. The precipitated TlCl was isolated by room temperature filtration and the desired products were obtained (yields 50–80%) by removal of the solvent in vacua. Characterisation was as for the compounds of FIG. 1.

By way of example, $Tl_4$ [1,4-(1-$C_6h_5$—$C_2B_9H_9)_2C_6H_4$] (196 mg, 0.15 mmol) was suspended in stirred thf (30 ml) under dry $N_2$ conditions, and $Cp_2ZrCl_2$ (88 mg, 0.30 mmol) was added. This immediately caused the formation of a white precipitate (TlCl), which turned grey on prolonged standing in air. After 30 minutes stirring, the purple solution was isolated by filtration and the thf removed in vacuo, yielding Bis-Zr(Cl)$_2$-1,4-(1-$C_6H_5$—$C_2B_9H_9)_2C_6H_4$.

Appearance: Purple powder
Yield: 94 mg, 67% IR (KBr disc; $v_{max}$): 3020 w (phenyl CH stretch), 2956 w (phenyl CH stretch), 2926 m (Cp CH stretch), 2856 m (Cp CH stretch), 2522 vs,br (BH stretch), 1472 vs,br (C═C stretch), 1446 vs,br (C═stretch), 1115 s (phenyl i.p.def.), 1016 m (phenyl i.p.def.), 720 s,br (BH stretch), 649 m (phenyl o.o.p.def.), 619 m (Phenyl o.o.p.def.). 558 m (C—H wag).
NMR ($CD_6D_6$): $^1H$ δ=0.9- c. 4.1 ppm (v.broad multiplet, BH), 3.96 (singlet, Cp H, 7.47 (broad multiplet, phenyl CH); $^{11}B$ δ=c. −40—+20 ppm (extremely broad signal, BH).
E.A Found C, 40.1; H, 4.5; $C_{42}B_{18}H_{52}Zr_2$ requires C, 40.4; H, 4.2.

Figure 5:
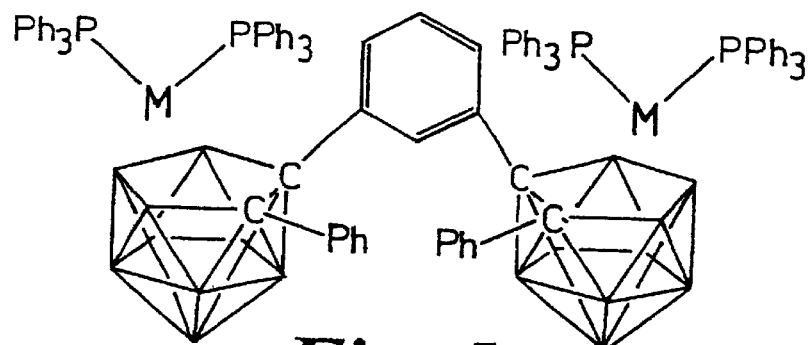

5) Compounds of the type shown in FIG. 5 were prepared by the reaction of the tetrathallium salt of Meta-Z-Compound (FIG. 8D) with two equivalents of $(Ph_3P)_2MCl_2$ (where M is Co, Pt, Pd) in dry THF at room temperature under nitrogen for 1 hour. The precipitated TlCl was removed by filtration and the desired products obtained by removal of the solvent in vacuo. Characterisation was as for the compounds of FIG. 1.

By way of example, $Tl_4$ [1,3-(1-$C_6H_5$—$C_2B_9H_9)_2C_6H_4$] (263 mg, 0.20 mmol) was suspended in stirred thf (40 ml) under ambient conditions, and brown $(PPh_3)_2CoI_2$ (336 mg, 0.40 mmol) was added. This immediately caused the formation of a white recipitate (TlCl), which turned grey on prolonged standing in air. After 30 minutes stirring, the green solution was isolated by filtration and the thf removed in vacuo, yielding Bis-Co$(PPh_3)_2$-1,4(1-$C_6H_5$—$C_2B_9H_9)_2C_6H_4$.

Appearance: Apple green powder
Yield: 269 mg, 81%
IR (KBr disc; $v_{max}$): 3054 w (phenyl CH stretch), 3024 vw (phenyl CH stretch), 3008 vw (phenyl CH stretch), 2497 s,br (BH stretch), 1636 S (?), 1618 s (?), 1437 s (C═C stretch), 1357 m (C═C stretch) 1121 s (phenyl i.p.def.), 1070 m (phenyl i.p.def.), 999 m (phenyl o.o.p.def. ?), 921 m (phenyl o.o.p.def.), 724 vs (BH stretch), 693 s BH stretch), 542 s (C—H wag).
Molar Magnetic Susceptibility ($\chi_M$): 2.68 BM
E.A. Found C, 67.7 5.8; $C_{94}H_{92}B_{18}P_4Co_2$ requires C, 68.1; H, 5.6.

Figure 6:
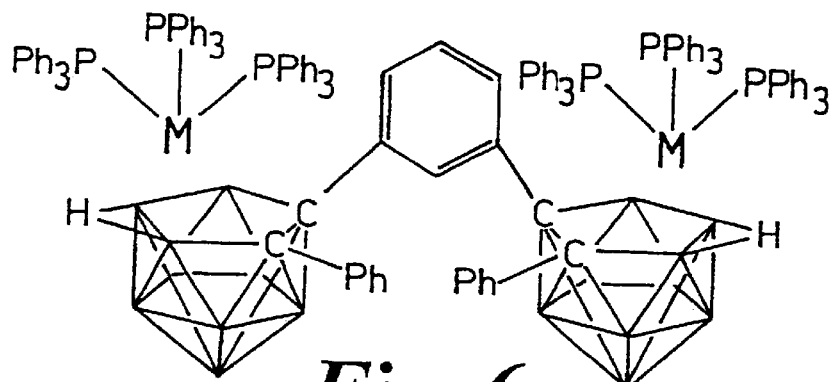

6) The compound shown in FIG. 6 (M is Rh) was prepared by reaction of the bi-potassium salt of the Meta-Z-Compound with two equivalents of $Rh(PPH_3)_3Cl$ in dry MeOH at room temperature under nitrogen for 1 hour. Precipitated TlCl was removed by filtration and the products isolated by removal of the solvent in vacuo (yield was approximately 40%). Characterisation was as for the compounds of FIG. 1.

Figure 7:
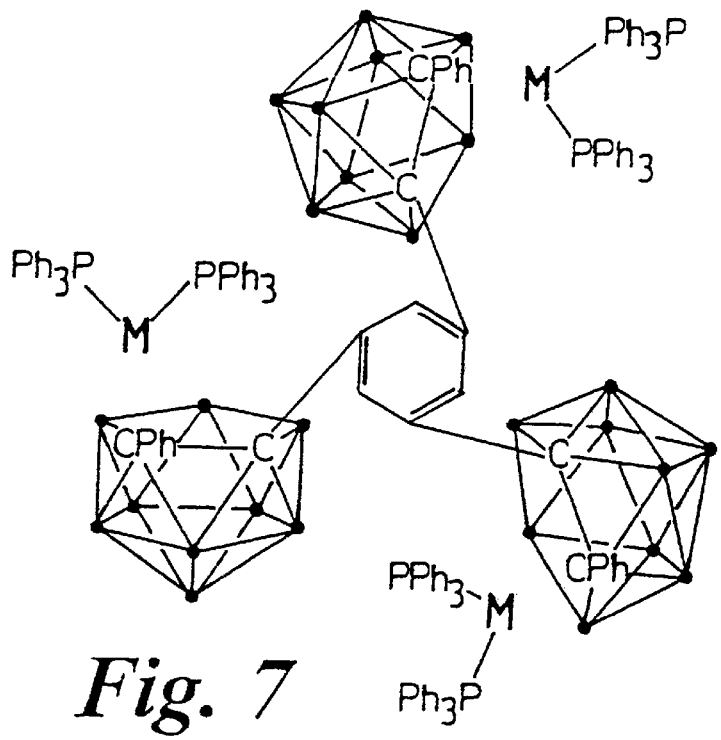

7) The compound of FIG. 7 was prepared by the reaction of the hexathallium salt of 1,3,5-(1-$H_5$—$C_2B_9H_9)_3C_6H_4$) with three equivalents of $(Ph_3P)_2MCl_2$ (M is Pd) in dry THF at room temperature under nitrogen for 1 hour. After filtering off precipitated TlCl, the solution was pumped to dryness giving the desired product in 65% yield. Characterisation was as for the compounds of FIG. 1.

By way of example, $Tl_6$ [1,3,5-(1-$C_6H_5$—$C_2B_9H_9)_3C_6H_3$] (192 mg. 0.10 mmol) was suspended in stirred thf (40 ml) under ambient conditions, and $(PPh_3)_2PdCl_2$ (140 mg, 0.20 m) was added. This immediately caused the formation of a white precipitate (TlCl), which turned grey on prolonged standing in air. After 30 minutes stirring, the purple solution was isolated by filtration and the thf removed in vacuo, yielding Tris-Pd$(PPh_3)_2$-1,3,5-(1-$C_6H_5$—$C_2B_9H_9)_3C_6H_3$.

Appearance: Purple powder
Yield: 211 mg, 53%
IR (KBr disc; $v_{max}$): 3055 w (phenyl CH stretch), 3026 w (phenyl CH stretch), 2962 vw (phenyl CH stretch), 2533 vs,br (BH stretch), 1481 m (C═C stretch) 1435 vs (C═C stretch), 1186 m (P—C stretch), 1119 m (phenyl i.p.def.), 1097 m (phenyl i.p.def.), 1066 m (phenyl i.p.def.), 1027 w (phenyl i.p.def.), 747 m (phenyl o.o.p.def.), 722 m (phenyl o.o.p.def.), 693 vs (BH stretch), 542 m (C—H wag), 519 m (C—H wag), 508 s (C—H wag),
NMR ($CDCl_3$): $^1H$ δ=0.7–3.7 ppm (v.broad multiplet B H̲), 7.38 (multiplet, phenyl CH̲); 7.41 (multiplet, phenyl CH̲, 7.49 (multiplet, phenyl CH̲, 7.66 (multiplet, phenyl CH̲); $^{11}B$ δ=−35 −+15 ppm (extremely broad signal, BH); $^{31}P$ δ=237.5 ppm (broad s, bound P̲Ph$_3$).
E.A. Found C, 63.2; H, 5.0, $C_{130}B_{27}H_{122}P_6Pd_3$ requires C, 64.4; H, 5.3

8) This example illustrates preparation of an actinide—containing compound. $Tl_4$ [1,4-(1-$C_6H_5$—$C_2B_9H_9$)$_2C_6H_4$] (261 mg, 0.20 mmol) was suspended in dry thf (30 ml) under anhydrous $N_2$ conditions. In a separate Schlenk tube dark green $UCl_4$ (152 mg, 0.40 mmol) was dissolved in a dry, degassed 1:4 mixture of HMPA and thf (25 ml). Addition of this solution to the original suspension (via cannula) caused the formation of a white precipitate (TlCl), which turned grey on prolonged standing in air. After 30 minutes stirring the green solution was isolated by filtration and the thf removed in vacuo, leaving a solution of Bis-$U(Cl_2)_2$-1,4-(1-$C_6H_5$—$C_2B_9H_9)_2C_6H_4$ in HMPA. The HMPA solvent was removed by repeated washing by water (3×20 ml), followed by removal of residual $H_2O$ in vacuo, giving pure Bis-$U(Cl_2$-1,4-(1-$C_6H_5$—$C_2B_9H_9)_2C_6H_4$ bis HMPA adduct.

Appearance: Light green powder

Yield: 170 mg, 58%

IR (KBr disc; $v_{max}$): 3018 w (phenyl CH stretch), 2956 m (methyl CH stretch), 2520 vs,br (BH stretch), 1488 m (C—N stretch) 1471 s (C—N stretch), 1448 s (C=C stretch), 1290 s, br (P=O stretch), 1113 s (phenyl i.p.def.), 1013 m (phenyl i.p.def.), 980 vs (P—N stretch), 721 vs,br (BH stretch), 620 m (phenyl o.o.p.def.), 555 m (C—H wag).

NMR ($C_6D_6$): $^1H$ $\delta$=0.9–4.0 ppm (v.broad multiplet, B$\underline{H}$, 2.39 (s, C$\underline{H}_3$), 7.45 (broad multiplet, phenyl C$\underline{H}$).

E.A. Found C, 27.5; H, 4.8; N, 5.7; $C_{34}B_{18}H_{68}N_6Cl_4P_2U_2$ requires C, 27.8; H, 4.7; N, 5.7

Metallacarboranes as catalysts

The compound of FIG. 2 where M is Rh was used as a catalyst in the hydrogen of cyclohexene to cyclohexene with hydrogen at room temperature and pressure. After 24 hours the percentage conversion was at least 95%. The solvent used was benzene. The catalyst was recovered and found to be unaltered and reusable.

The same catalyst was also used in the conversion of allylacetone to hexane-2-one with hydrogen. The conditions were as described above and it was found that there was greater than 95% conversion of the C=C bond whereas there was no conversion of the C=O bond.

The compound of FIG. 3 was used in a catalyst in the polymersation of ethene at room temperature and pressure. Two equivalents of methyl aluminoxane were added as co-catalyst. An amount of 5 mg catalyst was used. Although the reaction was not taken to completion, an amount of 253 mg polyethylene (mpt 136° C.) was obtained

What is claimed is:

1. A polynuclear compound comprising two or more carbon-bonded metal-hapto-3-capped nidocarborane groups.

2. A compound according to claim 1 wherein at least one other metal coordination site is filled by a monodentate ligand.

3. A compound according to claim 1 wherein the compound has an oligomeric or a cyclic structure.

4. A compound according to claim 1 wherein the compound includes two or three nidocarborane groups.

5. A compound according to claim 1 wherein two or more nidocarborane groups are linked together by a phenyl, pyridyl, triazyl, B(OH), CO, SO, $CH_2$, or B(Ph) group.

6. A compound according to claim 1 wherein the carborane units are substituted or linked in the 1,3, 1,4 or 1,5 (ie ortho, meta or para) positions.

7. A compound according to claim 1 wherein the metal is an F-block metal, Rh, Co, Mn, Ru, Pd, Fe, Ni, Pt, Cr, Mo or W.

8. A method of carrying out a chemical reaction in which a polynuclear compound comprising two or more metal-hapto-3-capped nidocarborane groups acts as a catalyst in the reaction.

9. A method according to claim 8, wherein the reaction is a hydrogenation reaction.

10. A method according to claim 9, wherein the compound is a rhodium compound.

11. A method according to claim 8, wherein the reaction is an oxidation reaction.

12. A method according to claim 11, wherein the compound is a uranium compound.

13. A method according to claim 8, wherein at least one other metal coordination site is filled by a monodentate ligand.

14. A method according to claim 8, wherein the compound has an oligomeric or a cyclic structure.

15. A method according to claim 8, wherein the compound includes two or three nidocarborane groups.

16. A method according to claim 8, wherein the two or more nidocarborane groups are linked together by a phenyl, pyridyl, triazyl, B(OH), CO, SO, $CH_2$, or B(Ph) group.

17. A method according to claim 8, wherein the carborane units are substituted or linked in the 1,3, 1,4, or 1,5 positions.

18. A method according to claim 8, wherein the metal is an F-block metal, Ph, Co, Mn, Ru, Pd, Fe, Ni, Pt, Cr, Mo, or W.

* * * * *